United States Patent [19]

Zepp et al.

[11] Patent Number: 5,258,517
[45] Date of Patent: Nov. 2, 1993

[54] METHOD OF PREPARING OPTICALLY PURE PRECURSORS OF PAROXETINE

[75] Inventors: Charles M. Zepp, Berlin; Yun Gao, Framingham; Donald L. Heefner, Hudson, all of Mass.

[73] Assignee: Sepracor, Inc., Marlborough, Mass.

[21] Appl. No.: 926,254

[22] Filed: Aug. 6, 1992

[51] Int. Cl.$^5$ .......................................... C07D 211/22
[52] U.S. Cl. ................................................... 546/240
[58] Field of Search .......................................... 546/240

[56] References Cited

U.S. PATENT DOCUMENTS

| | | | |
|---|---|---|---|
| 3,912,743 | 10/1975 | Christensen et al. | 260/293.58 |
| 4,007,196 | 2/1977 | Christensen et al. | 260/293.58 |
| 4,902,801 | 2/1990 | Faruk et al. | 546/220 |

FOREIGN PATENT DOCUMENTS

| | | | |
|---|---|---|---|
| 0223403 | 5/1987 | European Pat. Off. | 405/12 |
| 1422263 | 1/1976 | United Kingdom | 211/22 |

*Primary Examiner*—C. Warren Ivy
*Assistant Examiner*—Raymond Covington
*Attorney, Agent, or Firm*—Pennie & Edmonds

[57] ABSTRACT

A biocatalytic method of preparing optically pure precursors of paroxetine and a method of preparing paroxetine therefrom are disclosed. A racemic trans ester precursor compound of paroxetine is first prepared. The racemic trans ester precursor compound comprises a mixture of (3S,4R) and (3R,4S) enantiomers. The (3R,4S) enantiomer is hydrolyzed biocatalytically to the corresponding (3R,4S)-trans carboxylic acid or alternatively, the (3S,4R) enantiomer is biocatalytically hydrolyzed the to (3S,4R)-trans carboxylic acid in a reaction catalyzed by a isolated enzyme or a microorganism. In the first instance, the unhydrolyzed (3S,4R) enantiomer is separated from the (3R,4S)-trans carboxylic acid, whereas in the second instance the (3S,4R)-trans carboxylic acid is separated from the unhydrolyzed (3R,4S) enantiomer. The (3S,4R) enantiomer obtained following the selective hydrolysis is reduced to form a (−)-trans-(3S,4R) primary alcohol precursor of paroxetine. Paroxetine is then formed from the (−)-trans-(3S,4R) primary alcohol precursor.

14 Claims, No Drawings

METHOD OF PREPARING OPTICALLY PURE PRECURSORS OF PAROXETINE

BACKGROUND OF THE INVENTION

1. Field of the Invention

The present invention relates to a biocatalytic method of preparing optically pure precursors of paroxetine, and more particularly, it relates to an improved method of resolving a first racemic precursor of paroxetine into a second, optically pure precursor of paroxetine. Additionally, the present invention relates to a method of preparing paroxetine, an optically pure compound, from a racemic precursor.

2. Description the Background Art

U.S. Pat. No. 4,007,196 and U.S. Pat. No. 4,902,801, both incorporated by reference herein, disclose compounds of formula I:

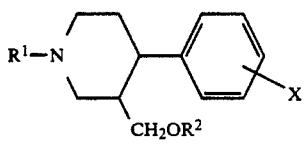

in which $R^1$ represents hydrogen, trifluoro ($C_{1-4}$) alkyl, alkyl or alkynyl, $R^2$ represents an alkyl or alkynyl group having 1-4 carbon atoms, or a phenyl group optionally substituted by $C_{1-4}$ alkyl, alkylthio, alkoxy, halogen, nitro, acylamino, methylsulfonyl or methylenedioxy groups. Alternately $R^2$ may represent a tetrahydronaphthyl group. X represents hydrogen, an alkyl having 1-4 carbon atoms, or an alkoxy, trifluoroalkyl, hydroxy, halogen, methylthio or aralkyloxy group.

The compounds of formula I have pharmacological properties that make them useful as anti-depressants. One compound that has proved especially valuable is the serotonin (5-HT) uptake inhibitor paroxetine [$R^1$=H, $R^2$=(1,3-benzodioxyl-5-yl), X=4-F], the pharmacologically active form of which is the (−)-trans isomer. The (−)-trans isomer (i.e., the active form) of paroxetine exhibits the (3S,4R) absolute stereoconfiguration according to Plenge et al. [*J. Pharm. Pharmacol.* 1987, 39: 877–882].

In U.S. Pat. No. 4,902,801 and U.S. Pat. No. 4,007,196, paroxetine is prepared from a (3S,4R)-trans precursor compound of formula (II):

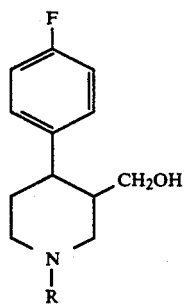

in which R is $CH_3$ or H. The piperidine carbinol compounds of formula (II) are in turn prepared by reduction of a racemic trans ester precursor compound of formula (III):

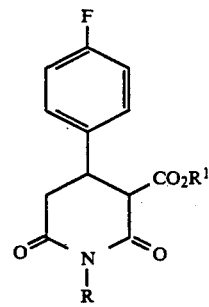

in which R is $CH_3$ or H and $R^1$ is $CH_3$ or $C_2H_5$. The reduction is carried out conventionally using a metal hydride, for example lithium aluminum hydride or aluminum hydride, in an inert solvent such as tetrahydrofuran or in a tetrahydrofuran/toluene mixture. Following reduction of the racemic trans ester precursor compound of formula (III), the precursor compounds of formula (II) are obtained in the trans configuration but as a mixture of (3R,4S) and (3S,4R) enantiomers. The precursor compounds of formula (II) are then resolved into their respective enantiomeric forms by conventional methods, such as diastereometric crystallization of salts with chiral acids such as, for example (+)-2′-nitrotartranilic acid or (−)-di-p-toluoyltartaric acid.

Paroxetine is prepared from the (3S,4R)-trans precursor compound of formula (II) making use of the procedures set out in U.S. Pat. No. 4,902,801 or U.S. Pat. No. 4,007,196.

This procedure has the disadvantage, however, that the diastereometric crystallization process is cumbersome and relatively expensive. Further, the reduction step, which is expensive, is performed prior to resolving the stereoisomers, thereby making it necessary to discard half of the expensive precursor compound of formula (II). In addition, since the carboxylate function is also reduced during the preparation of the precursor compound of formula (II), racemization and recycle of the (3R,4S) precursor compound of formula (II) is difficult.

Accordingly, there has been a need to prepare the precursor compound of formula (II) in a less cumbersome, less expensive manner.

SUMMARY OF THE INVENTION

An object of the present invention is to prepare the optically pure (3S,4R)-trans precursor compound of formula (II) from a racemic trans ester precursor compound of formula (III) without the disadvantages encountered in the prior art.

A further object of the present invention is to prepare paroxetine from an optically pure (3S,4R)-trans precursor compound of formula (II), which in turn is prepared from a racemic trans ester precursor compound of formula (III).

The present invention is directed to a method of preparing a trans compound of the formula

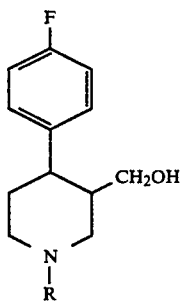

wherein R is CH₃ or H. The desired trans isomer exhibits the (3S,4R) absolute stereoconfiguration-that is, its structure is given by the formula

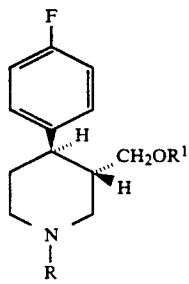

The method comprises preparing a racemic trans ester compound of formula

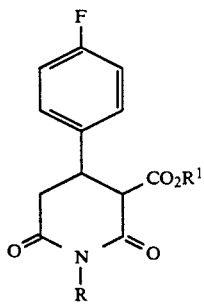

wherein R is CH₃ or H and R¹ is C₂H₅, said compound consisting of a mixture of (3R,4S) and (3S,4R) enantiomers. The (3R,4S) enantiomer of the racemic trans ester compound of formula (III) is biocatalytically and selectively hydrolyzed to the corresponding (3R,4S) carboxylic acid. The unhydrolyzed (3S,4R) enantiomer of the racemic trans ester compound of formula (III) is then separated from the (3R,4S) carboxylic acid (or isolated salt thereof) following which the desired (3S,4R) enantiomer is reduced to the (3S,4R)-trans compound of formula (II).

Alternatively, the (3S,4R) enantiomer is biocatalytically and selectively hydrolyzed to a (3S,4R)-trans carboxylic acid. The (3S,4R)-trans carboxylic acid is then separated from the unhydrolyzed (3R,4S) enantiomer (for example, by isolation in the form of a stable salt), following which the (3S,4R)-trans carboxylic acid is reduced to the (3S,4R)-trans compound of formula (II).

The present invention is also directed to a method of preparing paroxetine. The (3S,4R)-trans compound of formula (II) is prepared by either of the two aforementioned methods and reacted with thionyl chloride, benzenesulphonyl chloride, toluene sulfonylchloride or the like to form a first intermediate. The first intermediate is then reacted with sodium 3,4-methylenedioxyphenoxide. When R of the compound of formula (II) is methyl, a second intermediate, formed following reaction of the first intermediate with sodium 3,4-methylenedioxyphenoxide, is reacted with phenyl chloroformate, followed by deacylation with KOH.

DESCRIPTION OF THE PREFERRED EMBODIMENTS

The present invention is directed to the preparation of an optically pure (3S,4R)-trans precursor compound of formula (II) from a racemic trans ester precursor compound of formula (III) and to preparing paroxetine therefrom.

The method of the present invention for preparing an optically pure paroxetine precursor compound of formula (II) comprises preparing a racemic trans ester precursor compound of formula (III) as described in the Examples provided below. The racemic trans ester precursor compound of formula (III) is a mixture of (3R,4S) and (3S,4R) enantiomers. The (3R,4S) enantiomer is biocatalytically and selectively hydrolyzed to a (3R,4S)-trans carboxylic acid, after which case the (3S,4R) enantiomer is extracted from the (3R,4S)-trans carboxylic acid. The extraction may, for example, be carried out at a highly alkaline pH, in which case the acid will be present in its dissociated form. Thus, while the acid carries an electrical charge, the ester does not, and therefore the acid favors the aqueous phase whereas the ester favors the organic extraction phase. The (3S,4R) enantiomer is then reduced so as to form the (3S,4R)-trans precursor compound of formula (II).

Alternatively, the (3S,4R) enantiomer may be selectively hydrolyzed to the (3S,4R)-trans carboxylic acid by means of a biocatalyst—i.e., an enzyme or microorganism or genetically altered variations thereof. The (3S,4R)-trans carboxylic acid is then separated from the (3R,4S) enantiomer by extraction of one of the species. Alternatively, the (3S,4R)-trans carboxylic acid may be isolated from solution by formation of an insoluble and stable salt. In either event, removal of the (3S,4R)-trans carboxylic acid from solution should be effected as rapidly as possible so as to avoid decomposition of this somewhat unstable compound by decarboxylation. The (3S,4R)-trans carboxylic acid is then reduced so as to form the (3S,4R)-trans precursor compound of formula (II).

Preferably the racemic trans ester precursor compounds of formula (III) are prepared by reacting an alkyl malonamide of the formula

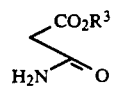

in which R₃ is CH₃ or C₂H₅, with methyl 4 fluorocinnamate to produce a precursor compound of the formula

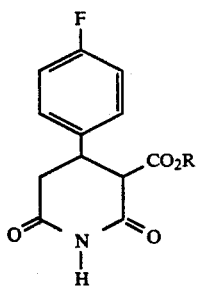

Alternatively, an alkyl-N-methyl malonamide of the formula

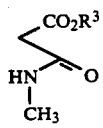

in which $R^3$ is $CH_3$ or $C_2H_5$ may be reacted with methyl-4-fluorocinnamate to produce a precursor compound of the formula

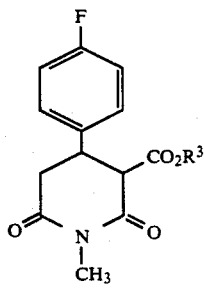

Particularly preferred as a precursor is the compound of the formula given immediately above wherein $R^3$ is methyl, i.e., the compound of formula II wherein both R and $R^1$ are $CH_3$:

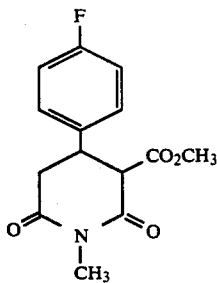

Moreover, in the preferred embodiment of the invention, the racemic trans ester precursor compound of formula (III) is a mixture of about 50% of the (3S,4R) enantiomer and about 50% of the (3R,4S) enantiomer.

The hydrolysis of the (3R,4S) enantiomer of the trans ester precursor compound of formula (III) is preferably carried out by a biocatalyst such as an enzyme or microorganism or genetically altered variations thereof which stereoselectively hydrolyzes the (3R,4S)-trans enantiomer. Alternatively, the hydrolysis of the (3S,4R) enantiomer of the trans ester precursor compound of formula (III) can be carried out by a biocatalyst which stereoselectively hydrolyzes the (3S,4R)-trans enantiomer.

More preferably, the biocatalyst which stereoselectively hydrolyzes the (3R,4S) enantiomer of the trans ester precursor compound of formula (III) is capable of attacking the carboxylic ester group of the (3R,4S)-trans enantiomer without attacking the carboxylic ester group of the (3S,4R)-trans enantiomer. Alternatively, the biocatalyst which stereoselectively hydrolyzes the (3S,4R) enantiomer of the trans ester precursor compound of formula (III) is capable of attacking the carboxylic ester group of the (3S,4R)-trans enantiomer without attacking the carboxylic ester group of the (3R,4S)-trans enantiomer.

The reduction of the (3S,4R) enantiomer of the trans ester precursor compound of formula (III) into the (3S,4R)-trans precursor compound of formula (II) may be performed by any method, such as, for example, catalytic hydrogenation, use of a metal hydride reducing agent, or by reaction with sodium metal in alcohol. Preferably the reduction is by use of a metal hydride reducing agent. The preferred metal hydride reducing agents are lithium aluminum hydride or aluminum hydride. It is further preferred that the metal hydride reducing agent be introduced in an inert solvent, such as, for example, tetrahydrofuran or a mixture of tetrahydrofuran and toluene.

The reduction of the (3S,4R)-trans carboxylic acid into the (3S,4R)-trans precursor compound of formula (II) may also be performed by any method, such as, for example, use of a metal hydride reducing agent. Preferably, the metal hydride reducing agent is lithium aluminum hydride. More preferably, the metal hydride reducing agent is disposed in an inert solvent, such as, for example, tetrahydrofuran or a mixture of tetrahydrofuran and toluene.

In one embodiment of the invention, those resolved enantiomers possessing the undesired (3R,4S) stereoconfiguration, namely, the (3R,4S) enantiomer of the trans ester precursor compound of formula (III) or the (3R,4S)-trans carboxylic acid—are discarded. Alternatively, they may be retained for subsequent treatment and recycle to the process where feasible.

The method of the invention for preparing paroxetine comprises preparing the (3S,4R)-trans precursor compound of formula (II) by either preferably reducing the (3S,4R) enantiomer of the trans ester precursor compound of formula (III) or, alternatively, by reducing the (3S,4R)-trans carboxylic acid formed by hydrolyzing the (3S,4R) enantiomer of the trans ester precursor of the compound of formula (III). The (3S,4R)-trans precursor compound of formula (II) is next reacted with thionyl chloride, benzenesulphonyl chloride, toluenesulfonylchloride, or any equivalent thereof. The intermediate thus formed is reacted with sodium 3,4-methylenedioxyphenoxide. When R of the (3S,4R)-trans precursor compound of formula (II) is methyl, the methyl group must be replaced with hydrogen in order to obtain the desired paroxetine compound. To do so, the intermediate formed after reaction with sodium 3,4-methylenedioxyphenoxide is reacted with phenyl chloroformate followed by deacylation with KOH. This removes the methyl group.

The foregoing and other objects, features, aspects and advantages of the present invention will become more apparent from the following detailed non-limiting examples of the present invention.

EXAMPLES

Example 1: Preparation of racemic trans ester precursor compounds of formula (III)

Preparation of methyl-4-fluorocinnamate

A one liter round bottom flask was charged with 50 grams (0.30 moles) of 4-fluorocinnamic acid, 500 milliliters of methanol, and 5.0 grams of concentrated sulfuric acid. This mixture was brought to reflux and kept there for 18 hours. After cooling, one half of the methanol was stripped under vacuum, and the remaining solution was poured into 600 milliliters of water. The precipitated solid was taken into 500 milliliters of diethyl ether and the aqueous phase was discarded. The ether solution was washed three times with 10% aqueous sodium hydroxide and once with water. After drying over magnesium sulfate, the mixture was filtered and stripped under vacuum to give methyl-4-fluorocinnamate as a white crystalline powder. Yield was 40 grams.

Preparation of ethyl malonamide

A one liter three neck flask containing 300 milliliters of methylene chloride was sealed with septa and weighed. After cooling to −20° C. in a dry ice-2-propanol bath, liquid ammonia was introduced until the weight increased by 10 grams. The flask was kept at −20° C. and was equipped with a paddle stirrer, addition funnel and thermometer. With stirring, a solution containing 25 grams (0.17 moles) of ethylmalonyl chloride in 50 milliliters of methylene chloride was slowly added through the addition funnel at a rate that kept the temperature below 0° C. The cooling bath was removed, and the slurry was stirred until it reached room temperature. The precipitated ammonium chloride was removed by filtration, and the filtrates were stripped under vacuum to provide an oil which solidified upon standing. The solid was recrystallized from a mixture of ethyl acetate and hexane to provide the ethyl malonamide as a white crystalline solid. Yield was 16 grams.

Preparation of the racemic trans ester precursor compound of formula III with R=H and R¹=C₂H₅

To a one liter three-neck round-bottom flask equipped with a stirrer, a nitrogen inlet and a thermometer, 13.8 grams (0.11 moles) of ethyl malonamide and 380 milliliters of dry tetrahydrofuran were added. This solution was purged with nitrogen and warmed to 30° C. in a water bath after which potassium tert-butoxide (10.1 grams, 0.09 moles) was added portionwise, with stirring, at a rate that kept the temperature below 35° C. To the resulting viscous slurry, 50 milliliters of dry dimethylsulfoxide was added to form a homogeneous solution. After cooling to 25° C., 13.9 grams (0.08 moles) of methyl-4-fluorocinnamate was added in one portion. Stirring was continued overnight, during which time a thick white slurry was formed. The slurry was diluted by the addition of 200 milliliters of diethyl ether followed by 300 milliliters of brine. The mixture was then treated with 1.0 normal phosphoric acid to bring its pH to 7.0. The aqueous layer was discarded and the organic layer was isolated, dried over magnesium sulfate, filtered, and stripped to give a clear colorless oil. Crystallization from 2-propanol gave the desired compound as a white powder. Yield was 17 grams. The reaction proceeded as shown below:

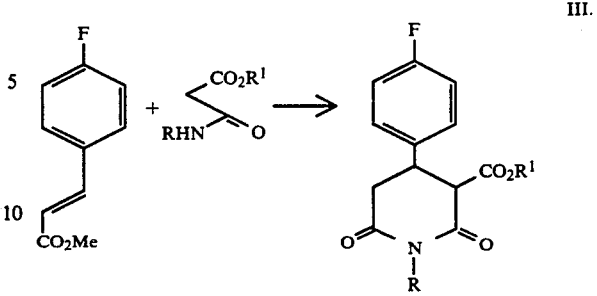

where R is hydrogen and R¹ is ethyl as hereinbefore described.

Preparation of ethyl-N-methyl malonamide

A 3 necked flask containing 400 ml. of diethyl ether was weighed and cooled to −20 deg. C., and liquid methylamine was added until there was a weight gain of 25 gm. The flask and contents were kept at −20 deg. C. by the use of a dry ice bath, and the flask was fitted with an overhead stirrer and an addition funnel. With stirring, a solution of ethylmalonyl chloride (50 gm.) dissolved in 50 ml. of diethyl ether was added at a rate that kept the temperature below 0 deg. C. After the addition was complete, the slurry was warmed to room temperature. The precipitate of methylamine hydrochloride was removed by filtration, and the filtrates were stripped to provide an oil which solidified upon standing. This solid was recrystallized from ethyl acetate/hexane to give 28 gm. of the desired compound.

Preparation of the racemic trans ester precursor compound of formula III with R=CH₃ and R¹=C₂H₅

A solution of ethyl-N-methyl malonamide (11.9 gm., 0.082 moles) dissolved in 50 ml. of dry DMSO was treated portion wise, while stirring under nitrogen, with sodium hydride (2.6 gm of an 80% dispersion, 0.087 moles). The resulting solution was treated in one portion with methyl-4-fluorocinnamate (11.0 gm., 0.061 moles) in 0 ml. of dry DMSO. This solution was stirred overnight, after which the DMSO solution was extracted once with hexane. The DMSO solution was poured into 35 ml. of water containing 5 ml. of acetic acid, and the oil which separated was taken into ethyl acetate. The ethyl acetate solution was washed once with brine, once with saturated sodium bicarbonate solution, and again with brine, after the solution was dried over magnesium sulfate. The drying agent was removed by filtration and the ethyl acetate was stripped to provide an oil smelling of DMSO. The oil was triturated in water and allowed to solidify overnight. This waxy solid was isolated and air dried before crystallization from a mixture of 2-propanol and hexane. Yield of the product was 17 gm.

Preparation of the racemic transester precursor compound of formula III with R=CH₃ and R¹=CH₃

A solution of ethyl-N-methyl malonamide (11.9 gm., 0.082 moles) was prepared under nitrogen in 100 ml. of absolute methanol. This solution was treated, in turn, with potassium tert-butoxide (9.8 gm., 0.087 moles) and methyl-4-fluorocinnamate (11.0 gm., 0.061 moles). The resulting solution was kept for one week with stirring at room temperature. After four days, a precipitate began to form. The slurry was poured into water containing 15 gm. of 85% phosphoric acid (solution pH=3.0), and the precipitated solid was extracted into ethyl acetate. The organic solution was extracted three times with water to remove a yellow colored impurity. The colorless organic solution was dried over magnesium sulfate, filtered and stripped to provide an oily solid. This was triturated in 50/50 ethyl acetate/hexane to give the desired product as colorless white crystals in yield of 9.2 gm.

Alternatively, the title compound may be prepared by the reaction of methyl-4-fluorocinnamate with methyl-N-methyl malonamide using reaction conditions and procedures similar to those set forth above for the corresponding ethyl-N-methyl malonamide reaction. The required methyl-N-methyl malonamide compound may be prepared from methylmalonyl chloride using reaction conditions and procedures substantially similar to those detailed above for the corresponding ethylmalonyl chloride reactant.

Example 2: Preparation of the (3S,4R)-trans precursor compound of formula (II)

The (3S,4R)-trans precursor compound of formula (II) can be prepared by two alternative methods. These methods are noted below as Method A and Method B.

Method A

The racemic trans ester precursor compound of formula (III) is substantially a 50/50 mixture of (3S,4R) and (3R,4S) enantiomers. The (3R,4S)-trans enantiomer of the ester precursor compound of formula (III) is hydrolyzed with the use of an enzyme which attacks the carbonyl group of the (3R,4S)-trans enantiomer without disturbing the carbonyl group of the (3S,4R)-trans enantiomer so as to form a mixture of a hydrolyzed (3R,4S)-trans carboxylic acid and the unhydrolyzed (3S,4R)-trans enantiomer of the ester precursor compound of formula (III). The unreacted (3S,4R)-trans enantiomer of the ester precursor compound of formula (III) is thereafter extracted from the hydrolyzed (3R,4S)-tarns carboxylic acid by solvent extraction at a high pH, following which the hydrolyzed (3R,4S)-trans carboxylic acid is discarded. The unreacted (3S,4R)-trans enantiomer of the ester precursor compound of formula (III) is then reduced into the (3S,4R)-trans enantiomer of the ester precursor compound of formula (III) is then reduced into the (3S,4R)-trans precursor compound of formula (II). The reaction proceeds as shown below:

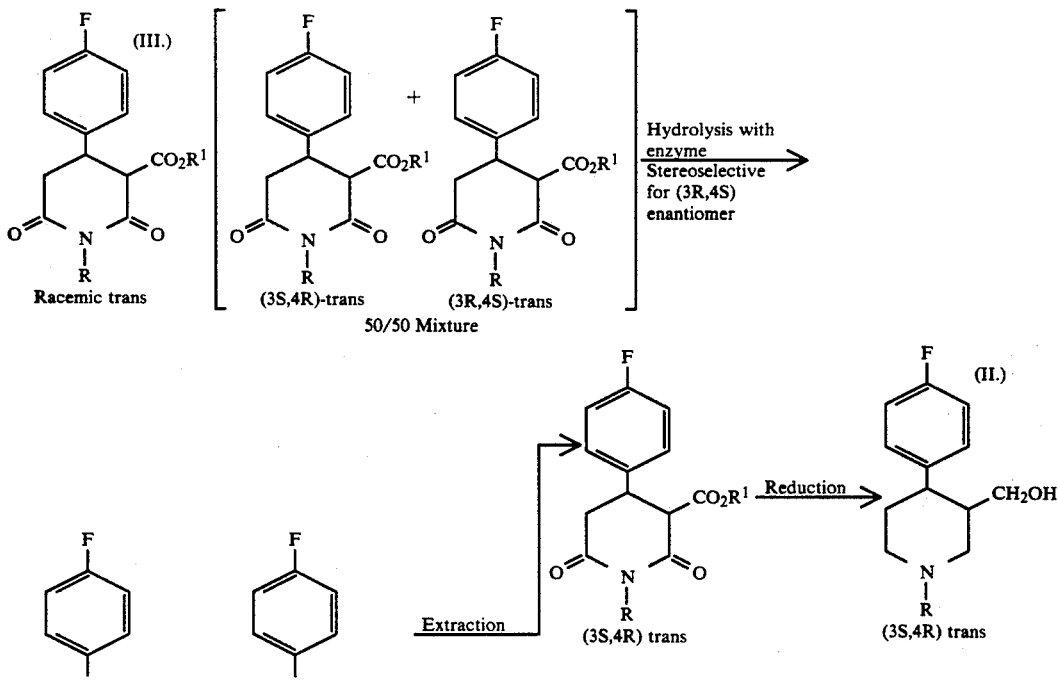

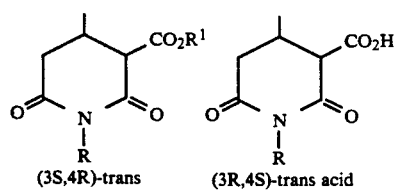
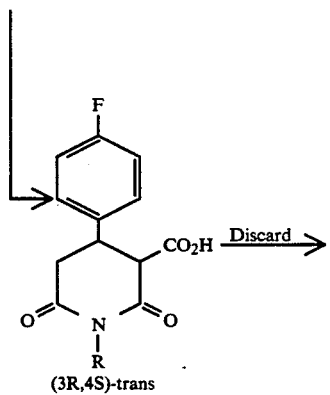

R and R¹ are as hereinbefore described.

Method B

The racemic trans ester precursor compound of formula (III) is, as noted in A above, substantially a 50/50 mixture of (3S,4R) and (3R,4S) enantiomers. In this method, an enzyme which stereoselectively hydrolyzes the (3S,4R)-trans enantiomer of the ester compound of formula (III) is used to form a mixture of a hydrolyzed (3S,4R)-trans carboxylic acid and the unhydrolyzed (3R,4S)-trans enantiomer of the ester precursor compound of formula (III). Thus, in contrast to Method A above, the enzyme chosen for use in this case is capable of attacking the carbonyl group of the (3S,4R)-trans enantiomer but does not attack the carbonyl group of the (3R,4S)-trans enantiomer. The hydrolyzed (3S,4R)-trans carboxylic acid is then separated from the unreacted (3R,4S)-trans enantiomer of the ester precursor compound of formula (III) by solvent extraction or isolation as a stable salt. The unreacted (3R,4S)-trans enantiomer of the ester precursor compound of formula (III) is discarded. The hydrolyzed (3S,4R)-trans carboxylic acid is subsequently reduced to the (3S,4R)-trans precursor compound of formula (II). The reaction proceeds as shown below:

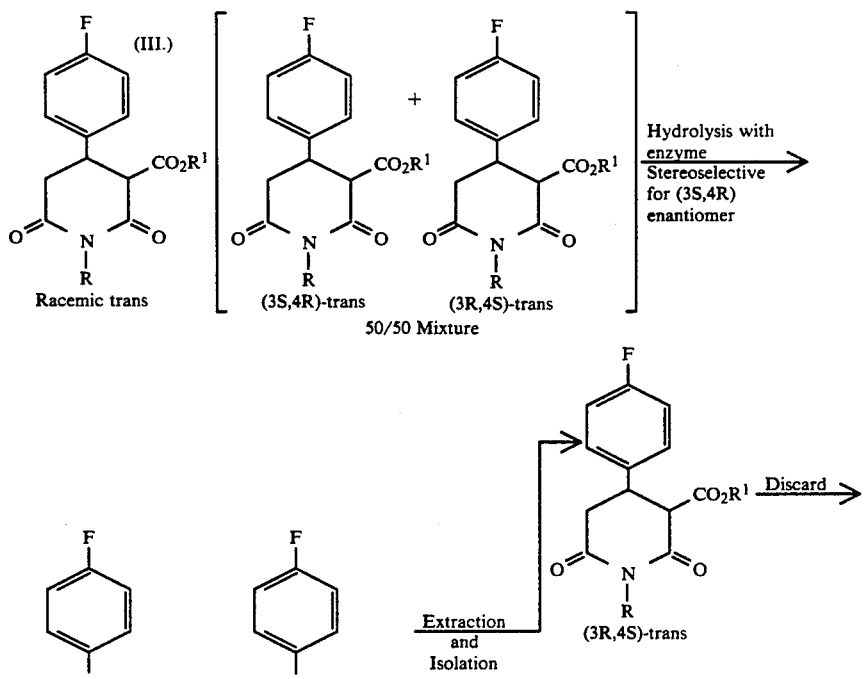

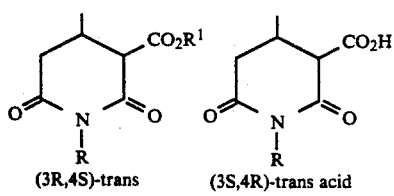
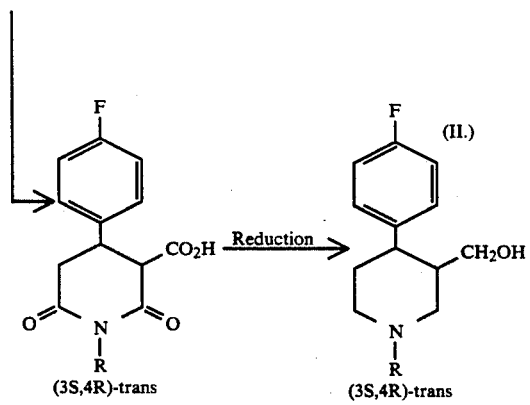

R and R[1] are as hereinbefore described.

Example 3: Identification of microorganisms that stereospecifically hydrolyze a racemic ester of the N-methyl precursor of Paroxetine (i.e., the Compound of formula III, R=CH₃, R¹=CH₃

Over 300 microorganisms were screened for stereospecific esterhydrolytic activity. This was done by first growing the cells in a narrow streak on solid media and then overlaying the streak with a warm 1% agarose (in 0.1M NaHPO₄, pH 7.0) solution containing a suspension of the racemic methyl ester of N-methyl paroxetine precursor (i.e., the compound of formula III with R=R¹=CH₃). The overlays were incubated at room temperature for periods up to several weeks. During the incubation period, the plates were periodically examined for zones of clearing around the microbial streak. Approximately 65 plates gave some indication of clearing.

These 65 cultures were then grown in liquid in the presence of racemic N-methyl paroxetine precursor. Over a period of several days, samples were taken and analyzed by chiral HPLC. The most active, most selective microorganism detected in our screens was an isolated Achromobacter sp. The test described above may be utilized to determine the stereospecific esterhydrolytic activity of any microorganism, including microorganisms other than those mentioned above, and thus their suitability for use in the process of the present invention.

Enzyme stereoselectivity was assessed by performing chiral HPLC on the ether extract of the reaction product mixture, which extract contains predominantly the unreacted trans-ester precursor in preference to the trans-carboxylic acid product upon hydrolysis. Chiral HPLC showed that one of the trans ester enantiomers had been stereoselectively hydrolyzed, producing an ester product characterized by an enantiomeric excess of 30% (as determined from the relative areas of the (3S,4R)- and (3R,4S)-ester peaks in the chromatogram). That peak which was first to elute on the Chiralcel OD column employed (2 runs using a 70/30 hexane/2-propanol mixture as the mobile phase at 0.75 ml/min) had the smaller peak area, demonstrating that it corresponds to the trans-ester enantiomer that is preferentially hydrolyzed by the particular Achromobacter. sp. discovered here. An enzyme useful for the purpose indicated may also be utilized by itself, i.e., without the microorganisms, e.g., such as where the enzyme may be synthetically produced. Subsequent experiments showed the optimum pH for hydrolysis to lie between 7 and 8.

Further workup of the organic extract yields a partially purified enantiomer of the compound of formula III wherein R and R' are both methyl. This enantiomer is chemically reduced to the corresponding compound of formula II by methods taught in this disclosure, and this latter compound of formula II is then converted still further to an optically enriched paroxetine entantiomer- the optical rotation of which is then determined by polarimetry. A positivelyrotating paroxetine enantiomer obtained in this manner is assigned the (3R,4S) stereoconfiguration and shows that the enzyme or microorganism employed in the resolution process is stereoselective for hydrolysis of the (3S,4R) enantiomer of the compound of formula III. On the other hand, the finding of a negative rotation for paroxetine enantiomer obtained in this manner demonstrates that the enzyme or microorganism is stereoselective for hydrolysis of the (3R,4S) enantiomer of the compound of formula III. This biocatalyst selectivity towards the (3R,4S) precursor is preferred, in as much as it permits the desired paroxetine end product to be obtained from the unconverted (3S,4R)-trans ester compound of formula III.

Example 4: Preparation of paroxetine

The (3S,4R)-trans precursor compound of formula (II) is reacted with a thionyl halide like thionyl chloride or a sulfonic acid halide like benzenesulphonyl chloride or toluenesulfonyl chloride as shown below to convert the alcohol to an alkylating agent and then further reacted with sodium 3,4-methylenedioxyphenoxide.

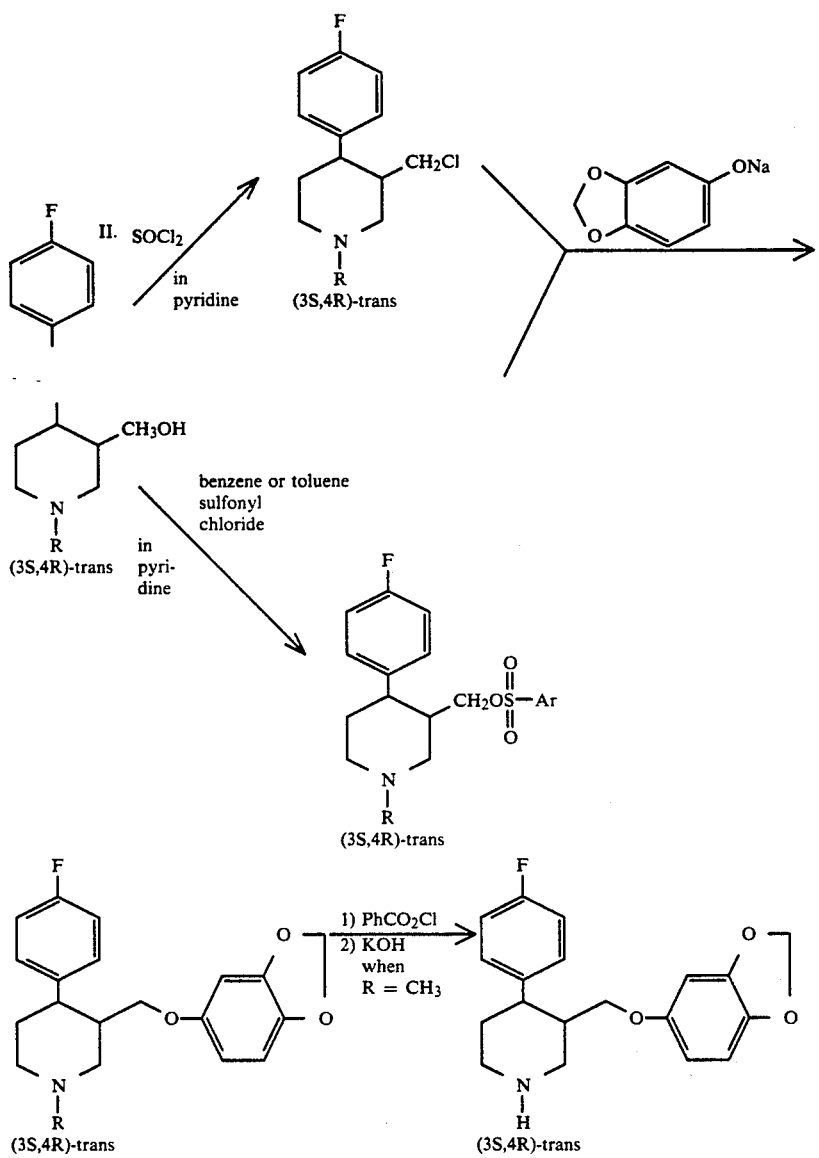

where Ar is an aromatic group derived from benzene or toluene sulfonic acid and R is as hereinbefore described. When R is Me, the N-methyl group is then replaced by reaction with phenyl chloroformate followed by de-acylation with KOH to obtain R=H.

With certain reagents and reaction conditions, derivatization at the amino function may also occur upon the first of the above-cited reaction steps. In such cases, the desired paroxetine compound with R=H may be recovered by methods known in the chemical arts—e.g., hydrolysis of the sulfonamide formed upon reaction of the compound of formula II with a sulfonyl chloride.

Although the present invention has been described in detail, it is clearly understood that the same is by way of example only and is not to be taken by way of limitation, the scope of the present invention being limited only by the terms of the appended claims.

What is claimed is:

1. A method of preparing an optically pure (3S,4R) compound of formula

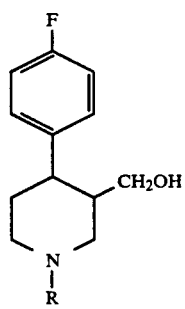

II.

wherein R is $CH_3$ or H, comprising the steps of:
(a) preparing a racemic trans ester compound of formula

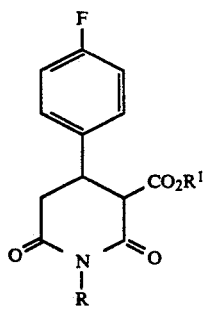

III.

wherein R is CH₃ or H and R¹ is CH₃ or C₂H₅, said racemic trans ester compound comprising a (3S,4R) enantiomer and a (3R,4S) enatiomer;

(b) selectively biocatalytically hydrolyzing said (3R,4S) enantiomer of said trans ester compound to a (3R,4S)-trans carboxylic acid using an enzyme, a microorganism or a generically altered variation thereof;

(c) separating said (3R,4R) enantiomer of said trans ester compound from said (3R,4S)-trans carboxylic acid; and (d) reducing said (3S,4R) enantiomer of said trans ester compound so as to form a (3S,4R)-trans compound of formula (II).

2. The method of claim 1, wherein said (3R,4S)-trans carboxylic acid is obtained by stereoselectively hydrolyzing said (3R,4S) enantiomer of said trans ester compound with a biocatalyst selected from the group consisting of an enzyme and a microorganism.

3. The method of claim 1, wherein said (3S,4R) enantiomer of said trans ester compound is separated from said (3R,4S)-trans carboxylic acid by solvent extraction.

4. The method of claim 1, wherein said (3S,4R) enantiomer is reduced to form compound (II) using a metal hydride reducing agent.

5. The method of claim 4, wherein said metal hydride reducing agent is lithium aluminum hydride.

6. A method of preparing an optically pure (3S,4R) compound of formula

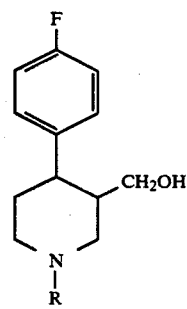

II.

wherein R is CH₃ or H, comprising the steps of:

(a) preparing a racemic trans ester compound of formula

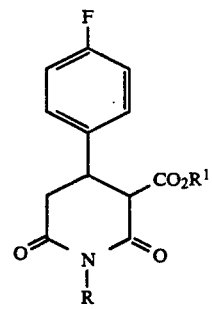

III.

wherein R is CH₃ or H and R¹ is CH₃ or C₂H₅, said racemic trans ester compound comprising a (3S,4R) enantiomer and a (3R,4S) enantiomer;

(b) selectively biocatalytically hydrolyzing said (3S,4R) enantiomer of said trans ester compound to a (3S,4R)-trans carboxylic acid using an enzyme, a microorganism or a genetically altered variation thereof;

(e) separating said (3S,4R)-trans carboxylic acid from said (3R,4S) enantiomer of said trans ester compound; and (f) reducing said (3S,4R)-trans carboxylic acid so as to form a (3S,4R)-trans compound of the formula (II).

7. The method of claim 6, wherein said (3S,4R)-trans carboxylic acid is obtained by stereoselectively hydrolyzing said (3S,4R) enantiomer of said trans ester compound with a biocatalyst selected from the group consisting of an enzyme and a microorganism.

8. The method of claim 6, wherein said (3S,4R)-trans carboxylic acid is separated from said (3R,4S) enantiomer of said trans ester compound by solvent extraction.

9. The method of claim 6, wherein said (3S,4R)-trans carboxylic acid is reduced to form compound (II) using lithium aluminum hydride.

10. The method of claim 6, wherein said (3S,4R)-trans carboxylic acid is reduced to form compound (II) using a metal hydride reducing agent.

11. A method of preparing paroxetine comprising the steps of:

(a) preparing a (3S,4R)-trans compound of formula

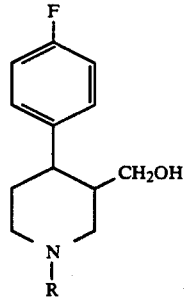

II.

wherein R is methyl, by the process of claim 1;

(b) reacting the compound of formula (II) wherein R is methyl with a compound selected from the group consisting of thionyl halides and sulfonic acid halides to form an intermediate wherein the alcohol is converted to an alkylating agent;

(c) reacting the intermediate formed by the reaction of step (b) with sodium 3,4-methylene-dioxyphenoxide; and (d) reacting the intermediate formed by the reaction of step (c) with phenyl chloroformate followed by de-acylation with KOH to replace the N-methyl group with hydrogen.

12. A method of preparing paroxetine comprising the steps of:

(a) preparing a (3S,4R)-trans compound of the formula

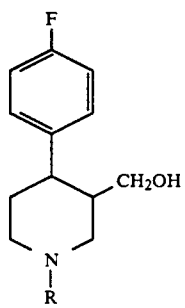

wherein R is hydrogen, by the process of claim 1;

(b) reacting the compound of formula (II) wherein R is hydrogen with a compound selected from the group consisting by thionylhalides and sulfonic acid halides to form an intermediate wherein the alcohol is converted to an alkylating agent; and (c) reacting the intermediate formed by the reaction of step (b) with sodium 3,4-methylenedioxy-phenoxide.

13. A method of preparing paroxetine comprising the steps of:

(a) preparing a (3S,4R)-trans compound of formula

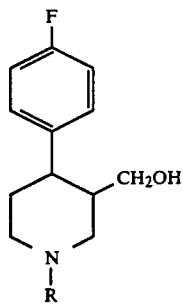

wherein R is methyl, by the process of claim 6;

(b) reacting the compound of formula (II) wherein R is methyl with a compound selected from the group consisting of thionyl halides and sulfonic acid halides to form an intermediate wherein the alcohol is converted to an alkylating agent;

(c) reacting the intermediate formed by the reaction of step (b) with sodium 3,4-methylenedioxy-phenoxide; and (d) reacting the an intermediate formed by the reaction of step (c) with phenyl chloroformate followed by de-acylation with KOH to replace the Nmethyl group with hydrogen.

14. A method of preparing paroxetine comprising the steps of:

(a) preparing a (3S,4R)-trans compound of formula

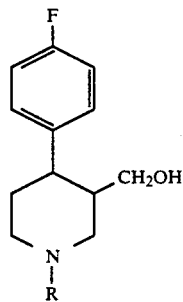

wherein R is hydrogen, by the process of claim 6;

(b) reacting the compound of formula (II) wherein R is hydrogen with a compound selected from the group consisting of thionyl halides and sulfonic acid halides to form an intermediate wherein the alcohol is converted to an alkylating agent; and (c) reacting the intermediate formed by the reaction of step (b) with sodium 3,4-methylene-dioxy-phenoxide.

* * * * *